US012563220B2

(12) United States Patent
Lai et al.

(10) Patent No.: US 12,563,220 B2
(45) Date of Patent: **\*Feb. 24, 2026**

(54) INHERITED MOTION INFORMATION FOR DECODING A CURRENT CODING UNIT IN A VIDEO CODING SYSTEM

(71) Applicant: HFI INNOVATION INC., Zhubei (TW)

(72) Inventors: Chen-Yen Lai, Hsinchu (TW);
Tzu-Der Chuang, Hsinchu (TW);
Ching-Yeh Chen, Hsinchu (TW);
Chih-Wei Hsu, Hsinchu (TW)

(73) Assignee: HFI INNOVATION INC., Zhubei (TW)

( \* ) Notice: Subject to any disclaimer, the term of this patent is extended or adjusted under 35 U.S.C. 154(b) by 108 days.

This patent is subject to a terminal disclaimer.

(21) Appl. No.: 18/662,882

(22) Filed: May 13, 2024

(65) Prior Publication Data

US 2024/0293940 A1 Sep. 5, 2024

Related U.S. Application Data

(60) Continuation of application No. 17/716,660, filed on Apr. 8, 2022, now abandoned, which is a division of
(Continued)

(51) Int. Cl.
*H04N 19/46* (2014.01)
*A61B 17/16* (2006.01)
(Continued)

(52) U.S. Cl.
CPC ............ *H04N 19/46* (2014.11); *B25J 9/1697* (2013.01); *B25J 13/08* (2013.01); *G06T 7/251* (2017.01);
(Continued)

(58) Field of Classification Search
CPC ..... A61B 17/1613; B25J 13/08; B25J 9/1697; G06T 2207/30204; G06T 7/251;
(Continued)

(56) References Cited

U.S. PATENT DOCUMENTS

| | | | |
|---|---|---|---|
| 7,965,773 B1 | 6/2011 | Schlanger | |
| 10,440,378 B1 | 10/2019 | Xu | |

(Continued)

FOREIGN PATENT DOCUMENTS

| | | |
|---|---|---|
| CA | 2950964 C | 10/2018 |
| CN | 103797799 A | 5/2014 |

(Continued)

OTHER PUBLICATIONS

Portuguese language office action dated Dec. 10, 2024, issued in application No. BR112021000004-6.
(Continued)

*Primary Examiner* — Anner Holder
(74) *Attorney, Agent, or Firm* — McClure, Qualey & Rodack, LLP

(57) ABSTRACT

A method of video decoding at a decoder can include receiving a bitstream including encoded data of a picture, decoding a plurality of coding units (CUs) in the picture based on motion information stored in a history-based motion vector prediction (HMVP) table, resetting the HMVP table for every N CTU rows. The method also provides updating the HMVP table with the motion information of the last Q of the plurality of CUs.

9 Claims, 6 Drawing Sheets

Related U.S. Application Data application No. 16/920,209, filed on Jul. 2, 2020, now Pat. No. 11,356,689, which is a continuation of application No. 16/503,758, filed on Jul. 5, 2019, now Pat. No. 10,743,016.

(60) Provisional application No. 62/699,761, filed on Jul. 18, 2018, provisional application No. 62/694,554, filed on Jul. 6, 2018.

(51) Int. Cl.

| | |
|---|---|
| *B25J 9/16* | (2006.01) |
| *B25J 13/08* | (2006.01) |
| *G06T 7/246* | (2017.01) |
| *G06T 7/73* | (2017.01) |
| *H04N 19/107* | (2014.01) |
| *H04N 19/139* | (2014.01) |
| *H04N 19/172* | (2014.01) |
| *H04N 19/436* | (2014.01) |
| *H04N 19/70* | (2014.01) |

(52) U.S. Cl.
CPC ............. *G06T 7/75* (2017.01); *H04N 19/107* (2014.11); *H04N 19/139* (2014.11); *H04N 19/172* (2014.11); *H04N 19/436* (2014.11); *H04N 19/70* (2014.11); *A61B 17/1613* (2013.01); *G06T 2207/30204* (2013.01)

(58) Field of Classification Search
CPC ...... G06T 7/75; H04N 19/107; H04N 19/139; H04N 19/172; H04N 19/436; H04N 19/46; H04N 19/52; H04N 19/70
See application file for complete search history.

(56) References Cited

U.S. PATENT DOCUMENTS

| | | | |
|---|---|---|---|
| 10,491,902 | B1 | 11/2019 | Xu |
| 2007/0206867 | A1 | 9/2007 | Tamura |
| 2011/0194609 | A1 | 8/2011 | Rusert et al. |
| 2011/0200107 | A1 | 8/2011 | Ryu |
| 2013/0101041 | A1 | 4/2013 | Fishwick |
| 2017/0127086 | A1 | 5/2017 | Lai |
| 2017/0332099 | A1 | 11/2017 | Lee et al. |
| 2018/0359483 | A1 | 12/2018 | Chen |
| 2020/0007889 | A1 | 1/2020 | Chao |
| 2020/0021839 | A1 | 1/2020 | Pham Van |
| 2020/0029085 | A1 | 1/2020 | Xu |
| 2020/0029088 | A1 | 1/2020 | Xu |
| 2020/0036997 | A1 | 1/2020 | Li |
| 2020/0045319 | A1 | 2/2020 | Xu |
| 2020/0059658 | A1 | 2/2020 | Chien |
| 2020/0077085 | A1 | 3/2020 | Zhang |
| 2020/0186820 | A1 | 6/2020 | Park |
| 2020/0186821 | A1 | 6/2020 | Park |
| 2020/0204820 | A1 | 6/2020 | Zhang |
| 2020/0260072 | A1 | 8/2020 | Park |
| 2020/0404342 | A1 | 12/2020 | Kotra |
| 2021/0014520 | A1 | 1/2021 | Zhang |
| 2021/0136405 | A1 | 5/2021 | Chen |
| 2021/0321092 | A1 | 10/2021 | Zhang |
| 2021/0337186 | A1 | 10/2021 | Zhang |
| 2021/0360228 | A1 | 11/2021 | Kotra |
| 2021/0409746 | A1 | 12/2021 | Wang |
| 2022/0007041 | A1 | 1/2022 | Li |
| 2022/0014782 | A1 | 1/2022 | Chon |

FOREIGN PATENT DOCUMENTS

| | | |
|---|---|---|
| CN | 103931196 A | 7/2014 |
| CN | 107925762 A | 4/2018 |
| CN | 110662052 A | 1/2020 |
| CN | 112534808 A | 3/2021 |
| CN | 112997486 A | 6/2021 |
| CN | 112997494 A | 6/2021 |
| EP | 2 755 389 A2 | 7/2014 |
| WO | WO 2013/039639 A1 | 3/2013 |
| WO | WO 2015/192780 A1 | 12/2015 |
| WO | WO-2016008409 A1 | 1/2016 |
| WO | WO2017/157249 A1 | 9/2017 |
| WO | WO 2018/105757 A1 | 6/2018 |
| WO | WO 2018/124957 A1 | 7/2018 |
| WO | 2020008346 A1 | 1/2020 |
| WO | WO 2020/003283 A1 | 1/2020 |
| WO | WO-2020018486 A1 | 1/2020 |
| WO | WO 2020/154147 A1 | 7/2020 |
| WO | WO-2020141915 A1 | 7/2020 |

OTHER PUBLICATIONS

English language office action dated Dec. 20, 2024, issued in application No. EP 19831286.0.

Zhang, Li, et al., "CE4-related: History-based Motion Vector Prediction", 11. JVET Meeting, Jul. 18, 2018, Ljubljana, (The Joint Video Exploration team of ISO/IEC JTC1/SC29/WG11 and ITU-TSG.16), No. JVET-<0104-v5, Jul. 10, 2018 to Jul. 8, 2018, XP030200019, 7 Pages (Year: 2018).

International Search Report and Written Opinion issued Oct. 10, 2019 in International Application No. PCT/CN2019/094873, 8 pages.

Combined Taiwanese Office Action and Search Report issued May 12, 2020 in Patent Application No. 108123742 (with English translation of Category of Cited Documents), 10 pages.

European Search Report issued Mar. 3, 2022 and Mar. 22, 2022 in European Application No. 19831286.0, 20 pgs.

Li Zhang, et al., "CE4-related: History-based Motion Vector Prediction", Joint Video Experts Team (JVET) of ITU-T SG. 16 WP 3 and ISO/IEC JTC1/SC 29/WG 11, 11$^{TH}$ Meeting: Ljubljana, SI, Jul. 10-18, 2018, 5 pgs.

C. C. Chen et al., "CE4-related: Shared merge list", Joint Video Experts Team (JVET) of ITU-T SG 16 WP 3 and ISO/IEC JTC1/SC 29/WG11, 12 Meeting; Macao, CN, Oct. 3-12, 2018, 4 pgs.

J. Li et al., "History-Based Motion Vector Prediction for Future Video Coding," 2019 IEEE International Conference on Multimedia and Expo (ICME), 2019, pp. 67-72, doi: 10.1109/ICME.2019.00020 (Year: 2019).

Zhang et al."CE4:History-based Motion Vector Prediction(Test4.4. 7)",Joint Video Experts Team(JVET)ofITU-TG16WP3and ISO/IECJTC1/SC29/WG11, 12thmeeting:Macao,CN,Oct. 3-12, 2018,DocumentJVET-L0O266-vOct. 12, 2018 (Year: 2018).

Zhang et al. "CE4:History-based Motion Vector Prediction(Test4. 4.7)", Joint Video Experts Team (JVET)ofITU-TG16WP3and ISO/IECJTC1/SC29/WG11, 12thmeeting:Macao,CN ,Oct. 3-12, 2018,DocumentJVET-L0266-vOct. 22, 2018 (Year: 2018).

L. Zhang, K. Zhang, H. Liu, Y. Wang, P. Zhao, and D. Hong, "CE4-related: History-based Motion Vector Prediction", JVET-K0104, Jul. 2018 (Year: 2018).

Chinese Office Action issued Mar. 31, 2023 in Chinese Application No. 201980044194.6, 8 pgs.

SLICE
501

CTU
502

511

512

513

514

520

CTU
602

TILE
601

611

612

613

614

620

*700*

START — S701

RECEIVE A BITSTREAM OF ENCODED VIDEO DATA — S710

DECODE A PLURALITY OF CODING UNITS WITHOUT UPDATING THE HMVP TABLE — S720

UPDATE THE HMVP TABLE WITH MOTION INFORMATION OF ALL OR A PART OF THE DECODED CODING UNITS — S730

RESET THE HMVP TABLE — S740

END — S799

INHERITED MOTION INFORMATION FOR DECODING A CURRENT CODING UNIT IN A VIDEO CODING SYSTEM

INCORPORATION BY REFERENCE

This present disclosure is a continuation application of U.S. application Ser. No. 17/716,660, "Inherited Motion Information for Decoding a Current Coding Unit in a Video Coding System" filed on Apr. 8, 2022 (now abandoned), which is a divisional application of U.S. application Ser. No. 16/920,209, "Inherited Motion Information for Decoding a Current Coding Unit in a Video Coding System" filed on Jul. 2, 2020 (U.S. Pat. No. 11,356,689), which is a continuation of U.S. application Ser. No. 16/503,758, "Inherited Motion Information for Decoding a Current Coding Unit in a Video Coding System" filed on Jul. 5, 2019 (U.S. Pat. No. 10,743,016), which claims the benefit of U.S. Provisional Application No. 62/699,761, "Inherited Motion Information for Improving Current CU Coding" filed on Jul. 18, 2018 and U.S. Provisional Application No. 62/694,554, "Inherited Motion Information for Improving Current CU Coding" filed on Jul. 6, 2018. The disclosures of the prior applications are hereby incorporated by reference in their entirety.

TECHNICAL FIELD

The present disclosure relates to video coding techniques.

BACKGROUND

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

Versatile Video Coding (VVC) standard is a next generation video compression standard being developed by the Joint Video Experts Team (JVET). VVC standard will be the successor to High Efficiency Video Coding (HEVC) standard. VVC aims to achieve 30%-50% better compression rate for the same perceptual quality compared with HEVC. The most promising among proposed video coding technologies have been incorporated in the draft VVC standard, while others are still under investigation.

SUMMARY

Aspects of the disclosure provide a method of video decoding at a decoder. The method can include receiving a bitstream including encoded data of a picture, decoding a plurality of coding units (CUs) in the picture based on motion information stored in a history-based motion vector prediction (HMVP) table without updating the HMVP table, and updating the HMVP table with motion information of all or a part of the plurality of CUs after the plurality of CUs are decoded based on the motion information stored in the HMVP table.

An embodiment of the method further includes decoding every P CUs in the picture based on motion information stored in the HMVP table without updating the HMVP table, P being an integer greater than 1, and updating the HMVP table with motion information of all or a part of every P CUs after every P CUs are decoded. In an example, a syntax element indicating a value of P is received in the bitstream, In an embodiment the decoding includes decoding CUs within a merge sharing region based on the motion information stored in the HMVP table. The plurality of CUs are the CUs within the merge sharing region that are decoded based on the motion information stored in the HMVP table. The updating includes, after the merge sharing region is decoded, updating the HMVP table with the motion information of all or the part of the CUs within the merge sharing region that are decoded based on the motion information stored in the HMVP table. The CUs within the merge sharing regions can be coded with a current picture reference (CPR) mode based on the HMVP table.

In an embodiment, the plurality of CUs are decoded in parallel.

In an embodiment, the updating includes one of updating the HMVP table with the motion information of the last Q of the plurality of CUs, Q being an integer greater than 0, updating the HMVP table with the last Q motion information of the remaining motion information of the plurality of CUs resulting from a pruning operation, updating the HMVP table with the motion information of the first W of the plurality of CUs, W being an integer greater than 0, or updating the HMVP table with the first W motion information of the remaining motion information of the plurality of CUs resulting from a pruning operation.

Embodiments of the method can further include resetting the HMVP table for every N coding tree unit (CTU) rows, N being an integer greater than 0. The N CTU rows can be CTU rows in a slice or a tile of the picture. In an embodiment, the HMVP table is reset for every CTU row in a slice or a tile of the picture. In an embodiment, the HMVP table is reset after processing N CTUs. N is an integer greater than 0. In an embodiment, the method further includes resetting the HMVP table after processing a region having a predefined size. In an embodiment, the HMVP table is reset at the beginning of a tile in the picture. In an embodiment, the HMVP table can be initialized at a beginning of a current CTU row without motion information of a CU in a CTU row processed prior to the current CTU row in the picture.

Embodiments of the method can include storing motion information of last CUs in a CTU row processed prior to a current CTU row in a buffer, and decoding the plurality of CUs in the current CTU row based on the motion information stored in the HMVP table and the buffer.

In an embodiment, a pruning process over a subset of HMVP candidates stored in the HMVP table can be performed. The subset of HMVP candidates is fewer than all the HMVP candidates in the HMVP table. The motion information for updating the HMVP table is not added to the HMVP table when an HMVP candidate in the HMVP table identical or similar to the respective motion information for updating the HMVP table is found.

Aspects of the disclosure provide an apparatus of video decoding. The apparatus can include circuitry configured to receive a bitstream including encoded data of a picture, decode a plurality of coding units (CUs) in the picture based on motion information stored in a history-based motion vector prediction (HMVP) table without updating the HMVP table, and update the HMVP table with motion information of all or a part of the plurality of CUs after the plurality of CUs are decoded based on the motion information stored in the HMVP table.

Aspects of the disclosure provide a non-transitory computer-readable medium storing a program. The program, when executed by a processor, causes the processor to perform the method of video decoding.

BRIEF DESCRIPTION OF THE DRAWINGS

Various embodiments of this disclosure that are proposed as examples will be described in detail with reference to the following figures, wherein like numerals reference like elements, and wherein.

DETAILED DESCRIPTION OF EMBODIMENTS

I. Video Encoder and Decoder

Figure 1:
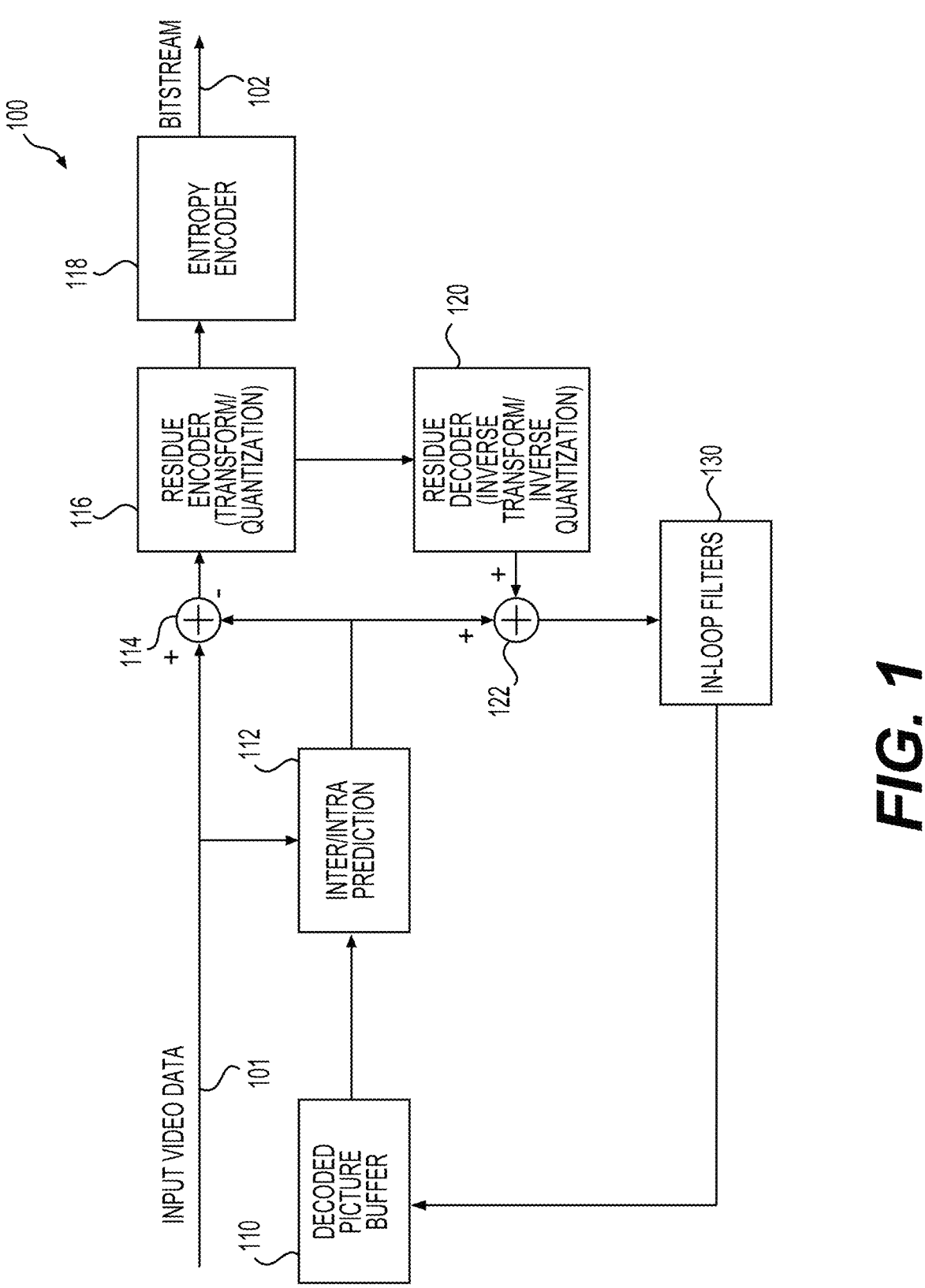
FIG. 1 shows an encoder according to an embodiment of the disclosure.

FIG. 1 shows an encoder 100 according to an embodiment of the disclosure. The encoder 100 can include a decoded picture buffer 110, an inter/intra prediction module 112, a first adder 114, a residue encoder 116, an entropy encoder 118, a residue decoder 120, a second adder 122, and one or more in-loop filters 130, such as a deblocking filter, a sample adaptive offset (SAO) filter, and an adaptive loop filter (ALF). Those components can be coupled together as shown in FIG. 1.

The encoder 100 receives input video data 101 and performs a video compression process to generate a bitstream 102 as an output. The input video data 101 can include a sequence of pictures. Each picture can include one or more color components, such as a luma component or a chroma component. A current picture (a picture currently under processing) can be divided into multiple coding units (CUs) with a same or different size for inter or intra prediction operations. The bitstream 102 can have a format compliant with a video coding standard, such as the Advanced Video Coding (AVC) standard, High Efficiency Video Coding (HEVC) standard, Versatile Video Coding (VVC) standard, and the like.

In some embodiments, in order to improve coding efficiency, the encoder 100 (e.g., the inter/intra prediction module 112) can be configured to process a current block (e.g., a CU currently under processing) based on motion information of previously coded blocks. For example, during an encoding process, CUs partitioned from a picture can be processed according a predefined order. A history-based motion vector prediction (HMVP) table can be employed to store non-duplicated motion information of blocks that are encoded prior to the current block. Each entry in such an HMVP table is referred to as an HMVP candidate.

When encoding the current block, the HMVP candidates can be used, for example, in a merge candidate list construction process when the current block is processed with a merge mode, or an advance motion vector prediction (AMVP) candidate list construction process when the current block is processed with an AMVP mode. For example, the HMVP candidates can be treated as motion candidates for the current block in addition to conventional spatial and temporal motion candidates during the merge candidate list or AMVP candidate list construction process. After the current block is processed, the determined motion information of the current block may be added to the HMVP table to update the HMVP table. In addition, the HMVP table can be reset (e.g., emptied), for example, at the beginning of a slice to avoid referencing motion vectors outside a current slice.

According to the disclosure, the encoder 100 (e.g., the inter/intra prediction module 112) can be configured to employ certain HMVP table updating and resetting techniques to enhance the above HMVP table based coding scheme. For example, instead of updating the HMVP table whenever an inter-coded CU is processed, the HMVP table can be updated after a set of CUs are processed. In this way, complexity of the updating operations can be reduced and operational cost can be lowered.

For example, in addition to resetting the HMVP at the beginning of a slice, the resetting can be performed after a smaller region has been processed. For example, the resetting can be performed after a number (e.g., 1, or 2) of coding tree unit (CTU) rows is processed. As a result, HMVP candidates would be limited in a local range of a picture near a current CU, which enhances the effect of referring HMVP candidates for coding motion information of the current CU.

In FIG. 1, the decoded picture buffer 110 is configured to store reference pictures that are useful for motion estimation and motion compensation performed at the inter/intra prediction module 112. The inter/intra prediction module 112 performs inter picture prediction or intra picture prediction to determine a prediction for a block of a current picture during the video compression process. The prediction of the block is provided to the first and second adders 114 and 122.

The first adder 114 receives a prediction of a block from the inter/intra prediction module 112 and original pixels of the block from the input video data 101. The adder 114 then subtracts the prediction from the original pixel values of the block to obtain a residue of the block. The residue of the block is transmitted to the residue encoder 116.

The residue encoder 116 receives residues of blocks, and compresses the residues to generate compressed residues. For example, the residue encoder 116 may first apply a transform, such as a discrete cosine transform (DCT), discrete sine transform (DST), wavelet transform, and the like, to the received residues corresponding to a transform block and generate transform coefficients of the transform block. Partition of a picture into transform blocks can be the same as or different from partition of the picture into prediction blocks for inter/intra prediction processing.

Subsequently, the residue encoder 116 can quantize the coefficients to compress the residues. The quantization can be controlled with a quantization parameter (QP). A QP indicates a step size for associating the transform coefficients with a finite set of steps.

The residue decoder 120 receives the compressed residues and performs an inverse process of the quantization and transformation operations performed at the residue encoder 116 to reconstruct residues of a transform block. Due to the quantization operation, the reconstructed residues are similar to the original residues generated from the adder 114 but typically are not the same as the original version.

The second adder 122 receives predictions of blocks from the inter/intra prediction module 112 and reconstructed residues of transform blocks from the residue decoder 120.

The second adder 122 subsequently combines the reconstructed residues with the received predictions corresponding to a same region in the picture to generate reconstructed video data. The reconstructed video data can then, for example, be transferred to the in-loop filters 130.

The in-loop filters 130 can include a deblocking filter that applies a set of low-pass filters to block boundaries to reduce blocking artifacts. The filters can be applied based on characteristics of reconstructed samples on both sides of block boundaries in a reconstructed picture as well as coding parameters (intra or inter coding modes, MVs, and QPs) determined at the inter/intra prediction module 112 or the residue encoder 116 in one example.

The in-loop filters 130 can include an SAO filter and an ALF. For example, the SAO filter receives the deblocked reconstructed video data from the deblocking filter and categorizes pixels in the reconstructed video data into groups. The SAO filter can then determine an intensity shift (offset value) for each group to compensate intensity shifts of each group. The shifted reconstructed video data can then be provided from the SAO filter to the ALF. In one example, the ALF is configured to apply a filter to reconstructed video data to reduce coding artifacts in the temporal domain. For example, the ALF selects a filter from a set of filter candidates and applies the elected filter to a region of the reconstructed video data. The processed reconstructed video data can then be transmitted to the decoded picture buffer 110.

The entropy encoder 118 receives the compressed residues from the residue encoder 116. The entropy encoder 118 may also receive other parameters and/or control information, such as intra prediction mode information, motion information, quantization parameters, control information from the in-loop filters, and the like. The entropy encoder 118 encodes the received parameters or other information to form the bitstream 102. The bitstream 102 including data in a compressed format can be transmitted to a decoder via a communication network, or transmitted to a storage device (e.g., a non-volatile computer-readable medium) where video data carried by the bitstream 102 can be stored.

Figure 2:
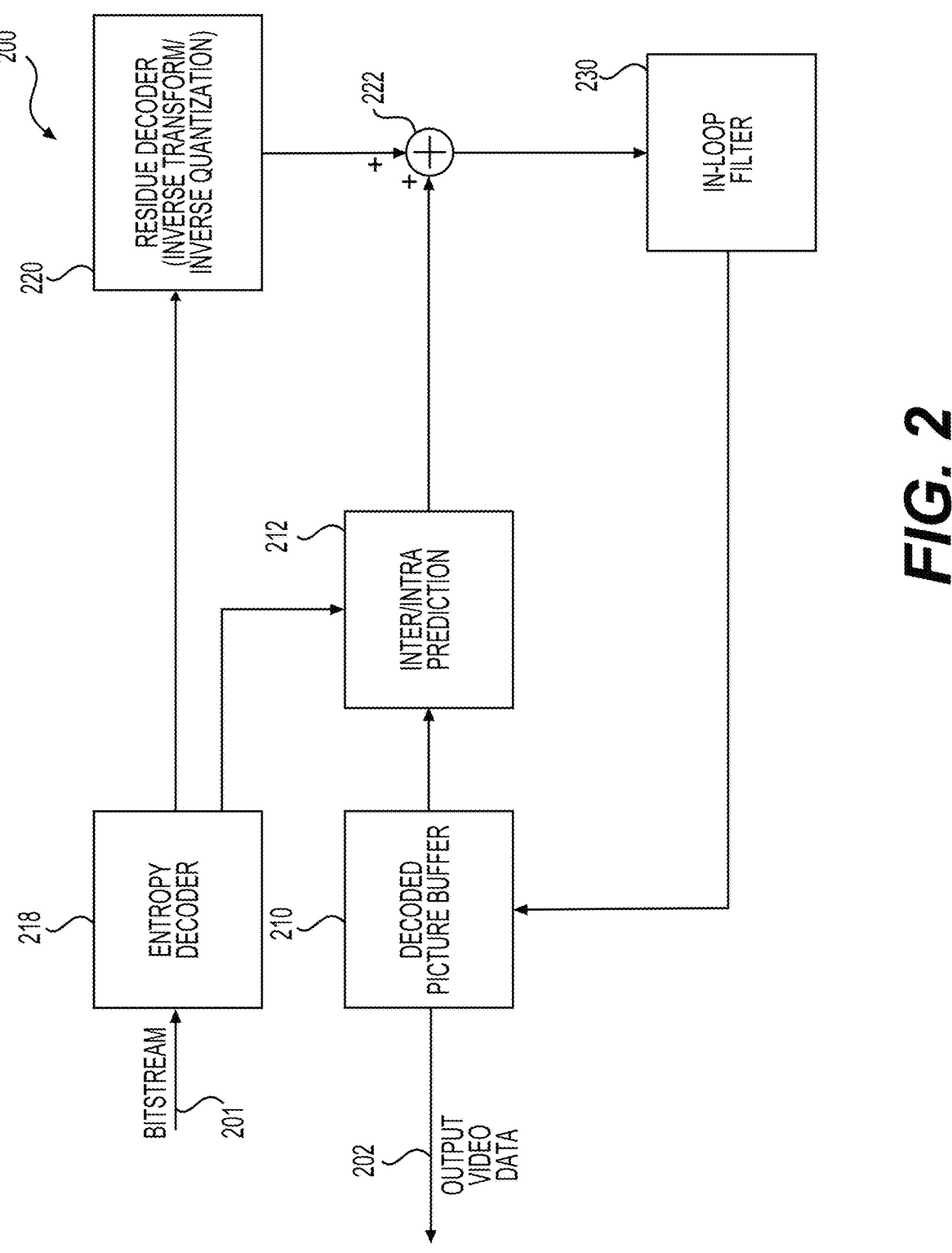
FIG. 2 shows a decoder according to an embodiment of the disclosure.

FIG. 2 shows a decoder 200 according to an embodiment of the disclosure. The decoder 200 includes an entropy decoder 218, a residue decoder 220, a decoded picture buffer 210, an inter/intra prediction module 212, an adder 222, and one or more in-loop filters 230, such as a deblocking filter, an SAO filter, and an ALF. Those components are coupled together as shown in FIG. 2. In one example, the decoder 200 receives a bitstream 201 generated by an encoder, such as the bitstream 102 generated by the encoder 100, and performs a decompression process to generate output video data 202. The output video data 202 can include a sequence of pictures that can be displayed, for example, on a display device, such as a monitor, a touch screen, and the like.

The decoder 200 (e.g., the inter/intra prediction module 212) can similarly be configured to process CUs using the HMVP table based coding scheme, and employ the HMVP table updating and resetting techniques to enhance the HMVP table based coding scheme. For example, during a decoding process, a HMVP table can be maintained to store non-duplicated motion information of previously decoded CUs. HMVP candidates can be used similarly in a merge candidate list construction process, or an AMVP candidate list construction process. Similarly, the HMVP table can be updated after a set of CUs has been decoded, and resetting of the HMVP table can be performed at the beginning of a smaller region than a slice (e.g., every CTU row). In this way, for the HMVP table based coding scheme, coding cost can be reduced.

In FIG. 2, the entropy decoder 218 receives the bitstream 201 and performs a decoding process which is an inverse process of the encoding process performed by the entropy encoder 118 in FIG. 1 example. As a result, compressed residues, prediction parameters (intra mode information, and motion information), in-loop filter control information, and the like, are obtained. The compressed residues are provided to the residue decoder 220, and the prediction parameters are provided to the inter/intra prediction module 212. The inter/intra prediction module 212 generates predictions of blocks of a picture based on the received prediction parameters, and provides the predictions to the adder 222. The decoded picture buffer 210 stores reference pictures useful for motion compensation performed at the inter/intra prediction module 212. The reference pictures, for example, can be received from the in-loop filters 230. In addition, reference pictures are obtained from the decoded picture buffer 210 and included in the picture video data 202 for displaying to a display device.

The residue decoder 220, the adder 222, and the in-loop filters 230 are similar to the residue decoder 120, the second adder 122, the in-loop filters 130 in terms of functions and structures.

In various embodiments, the encoder 100 and the decoder 200, or various modules or functions of the encoder 100 and decoder 200, can be implemented with hardware, software, or combination thereof. For example, the encoder 100 or the decoder 200 can be implemented with one or more integrated circuits (ICs), such as an application specific integrated circuit (ASIC), field programmable gate array (FPGA), and the like. For another example, the encoder 100 or the decoder 200 can be implemented as software or firmware including instructions stored in a computer readable non-transitory storage medium. The instructions, when executed by a processing circuit, causing the processing circuit to perform functions of the encoder 100 or the decoder 200.

It is noted that the HMVP table updating and resetting techniques described herein can be included in other decoders or encoders that may have similar or different structures from the encoder 100 or decoder 200. In addition, the encoder 100 and decoder 200 can be included in a same device, or separate devices in various examples.

II. History-Based Motion Vector Prediction (HMVP)

In various embodiments, an HMVP table, also referred to as an HMVP list or HMVP buffer, can store multiple HMVP candidates and is maintained during an encoding or decoding process. The HMVP table can be reset (e.g., emptied) at the beginning of each slice in a picture. Whenever there is an inter-coded block, motion information associated with the inter-coded block can be added as a last entry to the HMVP table.

Each HMVP candidate can be a set of motion information that, for example, includes horizontal and vertical displacements corresponding to one or two motion vectors, reference picture indices corresponding to the one or two motion vectors, and prediction direction information (e.g., reference picture list, L0 or L1) of the one or two motion vectors.

In an embodiment, a size of an HMVP table is set be L (e.g., 16), and up to L HMVP candidates can be added to the table. In an embodiment, when there are more than L HMVP candidates from previously coded blocks, a first-in-first-out (FIFO) rule is applied to update the HMVP table. As a result, the HMVP table contains the latest previously coded L motion candidates.

In an embodiment, when adding a new HMVP candidate, a redundancy check process is performed to search for an HMVP candidate identical or similar to the new HMVP candidate. If an identical or similar HMVP candidate is found, the identical or similar HMVP candidate is removed from the HMVP table, and all HMVP candidates following the removed one are moved forward. The new HMVP candidate is then added as a last entry of the HMVP table.

A. AMVP Mode and Merge Mode as Specified in HEVC

To implement the HMVP table based coding scheme, an HMVP table can be combined with an AMVP mode or a merge mode as specified in HEVC standards in various embodiments.

For example, when coding a CU with the AMVP mode at an encoder side, an AMVP candidate list can first be constructed. For example, the following three types of motion vector prediction (MVP) candidates can be checked in order: spatial MVP candidates; temporal MVP candidates; and zero MVP candidates. A motion compensation process can then be performed to determine a real motion vector for the CU. Thereafter, a MVP candidate can be selected from the AMVP candidate list to be a MVP of the real motion vector. As a result, a difference between the real motion vector and the selected MVP candidate, and a MVP index referring to the selected MVP candidate in the AMVP candidate list can be signaled to a decoder side.

At the decoder side, when decoding the CU, an AMVP candidate list can be constructed the same way as at the encoder side. Based on the signaled MVP index, an MVP candidate the same as the one selected at the encoder side can be determined. By combining the MVP candidate with the signaled difference, a motion vector can be reconstructed that is the same as the real motion vector at the encoder side.

Similarly, when coding a CU with the merge mode at an encoder side, a merge candidate list can first be constructed by checking the following four types of merge MVP candidates: spatial merge candidates; temporal MVP merge candidates; combined bi-predictive merge candidates; and zero motion vector merge candidates. For example, the four types of candidates are checked sequentially, and when available, added to the merge candidate list until a maximum allowed number of candidates in the merge candidate list is reached. The merge candidates in the merge candidate list can then be evaluated to optimally select a candidate, and a merge index referring the selected candidate can be determined and subsequently signaled to a decoder side.

At the decoder side, when decoding the respective CU, a merge candidate list can be constructed in a way the same as at the encoder side. Then, with the merge candidate list, a merge candidate can be determined based on the signaled merge index. Accordingly, motion information associated with merge candidate can be inherited for determining a prediction block of the respective CU.

B. Using HMVP Table in Combination with AMVP Mode and Merge Mode

In an embodiment, an HMVP table is used in combination with the AMVP mode, and HMVP candidates are used in the AMVP candidate list construction process. In one example, the last K HMVP candidates are inserted in the AMVP candidate list after the temporal MVP candidates are checked. For example, K can be set to be 4. Only HMVP candidates with the same reference picture as an AMVP target reference picture of a current CU are used to construct the AMVP candidate list of the current CU. A pruning process may be performed over the AMVP candidate list when adding the HMVP candidates. For example, if an AMVP candidate on the AMVP candidate list identical or similar to a to-be-added HMVP candidate is found in the AMVP candidate list, the to-be-added HMVP candidate may not be added to the AMVP candidate list.

In an embodiment, an HMVP table is used in combination with the merge mode, and HMVP candidates are used in the merge candidate list construction process. In one example, all the HMVP candidates are inserted to the merge candidate list after the temporal merge candidates are checked. Similarly, a pruning process may be performed over the merge candidate list when adding the HMVP candidates.

In the above two embodiments, after the current CU is processed, the associated motion information of the current CU is added to the HMVP table to update the HMVP table.

While the AMVP mode and merge mode are used as examples to illustrate how an HMVP table is operated in a coding mode, coding modes employing an HMVP table are not limited to the AMVP mode or merge mode. For example, triangle partition mode, current picture reference (CPR) mode (also referred to as intra block copy (IBC) mode), and the like, can also be performed in combination with an HMVP table.

III. HMVP Table Updating and Resetting Techniques

In the HMVP table based coding scheme, an HMVP table can be employed to provide motion information of previously processed inter-coded blocks for encoding or decoding a current CU. During an encoding or decoding process based on the HMVP table, after an inter-coded block is processed, the HMVP table is updated with motion information associated with the inter-coded block. When a slice of a picture begins, the HMVP table is emptied. As a result, reference to HMVP candidates is limited within a range defined by the slice. Some updating and resetting techniques can be employed to enhance the HMVP table based coding scheme.

A. HMVP Table Updating Techniques

Instead of updating an HMVP table whenever an inter-coded block is processed, the updating operation can be performed after a set of blocks or a predefined region of blocks is processed in some embodiments.

Figure 3:
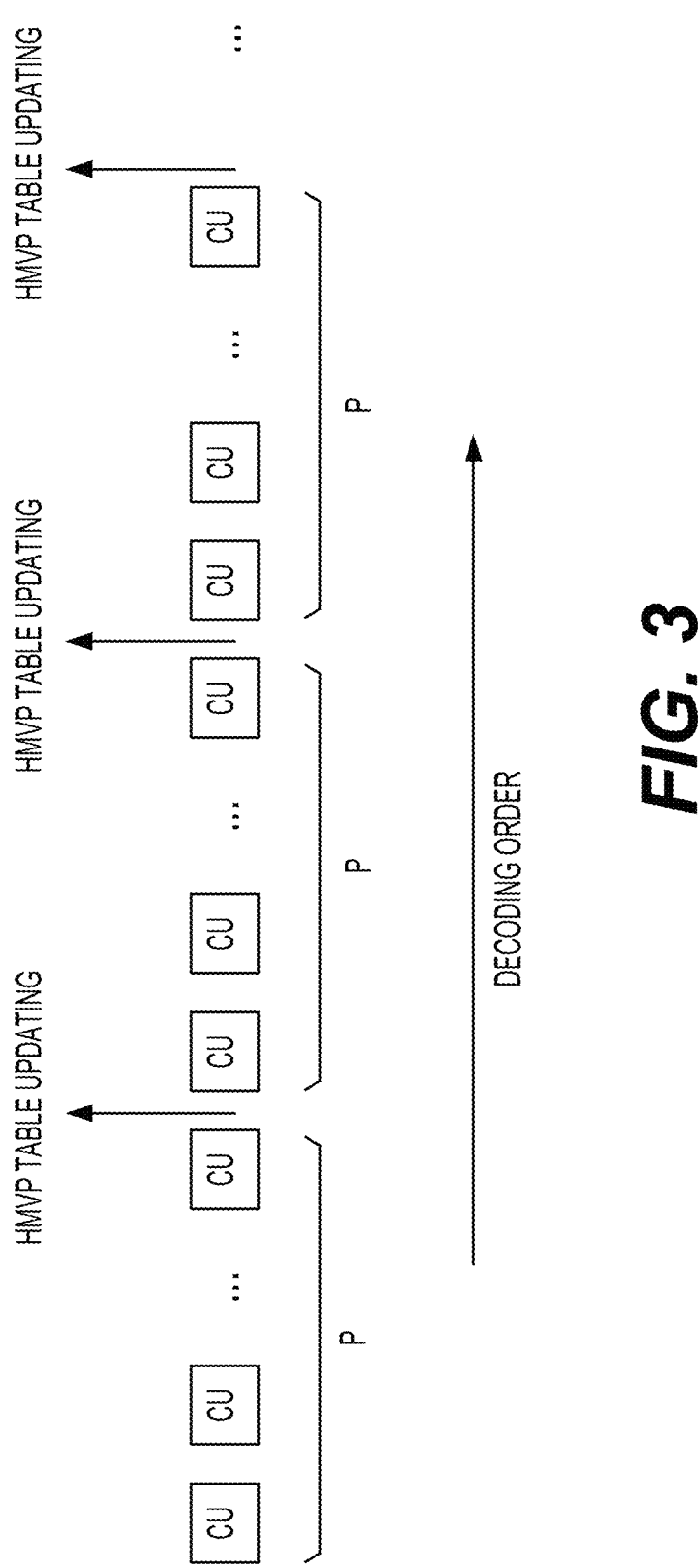
FIG. 3 shows an example of performing history-based motion vector prediction (HMVP) table updating for every P number of CUs according to an embodiment of the disclosure.

In some embodiments, an HMVP table is updated after a number of CUs are decoded. For example, the number can be an integer, denoted by P, that is greater than 1. P can be equal to 2, 3, 4, and the like. Accordingly, the HMVP table can be updated after every 2, 3, or 4 CUs are decoded. FIG. 3 shows an example of performing HMVP table updating for every P number of CUs according to an embodiment of the disclosure. The value of P can be predefined or can be signaled with a syntax element at sequence level, picture level, slice level, tile group level, tile level, or the like. In an example, when signaling a value of P, P can be an integer greater than 1 or equal to 1. In this way, by configuring P, HMVP table updating can be performed either for each inter-code block, or for every group of P inter-coded blocks.

In a first embodiment, the P number of CUs are CUs each processed based on the HMVP table. For example, the P number of CUs are each coded with an inter picture coding mode that is performed in combination with the HMVP table. Different members of the P number of CUs may be processed with different inter picture coding modes. For example, when a sequence of CUs including the P number of CUs are processed according to a predefined decoding order, the P number of CUs can be interleaved or mixed with other CUs that are coded without using the HMVP table, or the P number of CUs can be successively processed without being interleaved or mixed with other CUs that are coded without using the HMVP table.

Typically, in an inter picture coding mode, one or more motion vectors, that are displacements with respect to a current block, can be employed to determine one or more prediction blocks in reference pictures for coding the current block. Those one or more motion vectors can be predictedly coded using motion information of blocks coded prior to the current block. Motion information stored in an HMVP table can be employed to supply the motion information needed for coding the motion information of the current block. Examples of the inter picture coding mode can include AMVP mode, merge mode, triangle partition mode, CPR mode (IBC mode), or the like.

In a second embodiment, the P number of CUs each may or may not be processed based on the HMVP table. For example, among the P number of CUs, a CU may be coded with a coding mode where the HMVP table is not employed. For example, the CU is coded with an intra mode, and no motion information is generated when coding the CU. For example, under certain scenarios, an inter picture coding mode may operate without using the HMVP table (e.g., combination with the HMVP table is turned off). Accordingly, when coding a sequence of CUs partitioned from a picture, CUs coded with reference to the HMVP table and CUs coded without reference to the HMVP table can be interleaved or mixed.

When updating the HMVP table for every P number of CUs, all motion information associated with the CUs coded based on the HMVP table can be used to update the HMVP table. Alternatively, a subset of all motion information associated with the CUs coded based on the HMVP table can be used to update the HMVP table.

In an embodiment, only motion information of the last Q CUs coded with the HMVP table is used to update the HMVP table. For example, P is equal to 4, and the 4 CUs are coded successively with the HMVP table. However, only motion information of the last 2 CUs is used to update the HMVP table. In this way, computation cost associated with updating the HMVP table can be reduced compared with updating the HMVP table with motion information of 4 CUs.

In an embodiment, the motion information of the CUs coded with HMVP table may first be pruned to remove the motion information that is identical or similar to other motion information. For example, a similarity between motion information may be evaluated based on a similarity threshold. Then, only the last Q motion information of the remaining motion information resulting from the pruning is used to update the HMVP table.

In an embodiment, only motion information of the first W CUs coded with the HMVP table is used to update the HMVP table. For example, P is equal to 3, and the 3 CUs are coded successively with the HMVP table. However, only motion information of the first CU is used to update the HMVP table. Similarly, computation cost associated with updating the HMVP table can be reduced compared with updating the HMVP table with motion information of 3 CUs.

In an embodiment, similarly, a pruning operation may first be performed over the motion information of the CUs coded with HMVP table to remove the motion information that is identical or similar to other motion information. Then, only the first W motion information of the remaining motion information resulting from the pruning operation is used to update the HMVP table.

In some embodiments, an HMVP table is updated when a region in a picture is decoded. In various embodiments, the region may be defined differently. CUs within such a region each may or may not be processed with a coding mode that employs the HMVP table.

In one example, a region, for example, with a square or rectangular shape can be defined for pipeline processing where a picture may partitioned into such regions that are sequentially fed to a pipeline processing circuit. A size of the region (e.g., 32×32 or 64×64 pixels) can be suitably defined to fit with the pipeline.

In one example, the region is defined to be a merge sharing region. For example, a CTU may be portioned based on a tree-structured split scheme. A merge sharing region can correspond to an ancestor node (referred to as a merge sharing node) in a CU split tree which is partitioned into a set of leaf CUs. The merge sharing region can be treated as a CU, and a merge candidate list can accordingly be constructed for this CU (the merge sharing region). The merge candidate list can be shared among the leaf CUs that are coded with a merge list based coding mode, such as a merge mode, a CPR mode (or IBC mode), a triangle partition mode, and the like. In this way, computation cost associated with merge list construction can be reduced, and parallel processing of the leaf CUs can be applied.

Figure 4:
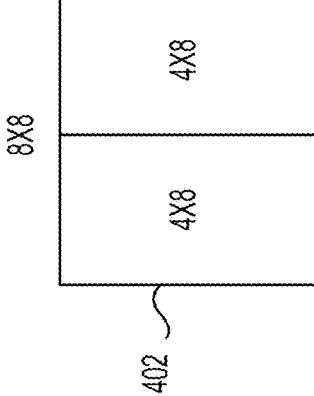
FIG. 4 shows examples of merge sharing regions according to an embodiment of the disclosure.
Figure 4:
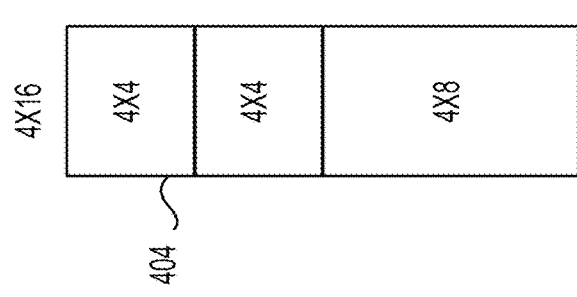
Figure 4:
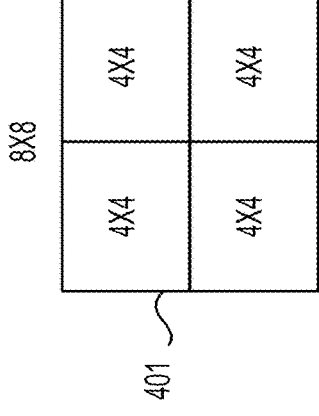
Figure 4:
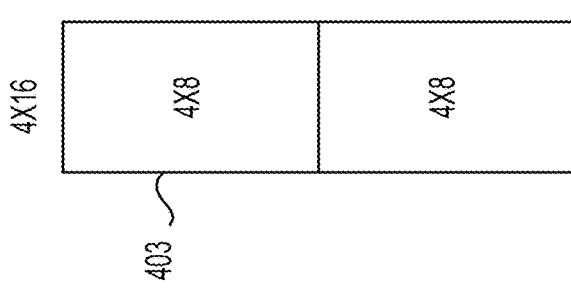

FIG. 4 shows examples of merge sharing regions according to an embodiment of the disclosure. In FIG. 4 example, a merge sharing region is defined to be a region having a size equal to or smaller than a threshold (e.g., 64 pixels). Accordingly, in FIG. 4, a first merge sharing region 401 includes 4 leaf CUs each having a size of 4×4 pixels. A second merge sharing region 402 includes 2 leaf CUs each having a size of 4×8 pixels. A third merge sharing region 403 has 2 leaf CUs each having a size of 4×8 pixels but arranged vertically. A fourth merge sharing region 404 has 3 leaf CUs having sizes of 4×4 pixels, 4×4 pixels, and 4×8 pixels, respectively.

It is noted that a merge sharing region may be defined differently from the FIG. 4 example in other examples. For example, a merge sharing region is defined to be a region that has a size equal to or larger than a threshold and includes at least one leaf CU having a size smaller than the threshold. In addition, in some examples, a leaf CU within a merge sharing region may be processed with a mode other than the merge list based merge mode. For example, the leaf CU may be processed with an intra mode, an AMVP mode, an affine mode, and the like. Accordingly, the processing of such a leaf CU does not use motion information from an HMVP table.

When an HMVP table is used for processing a region, the HMVP table can accordingly be updated after CUs within the region are processed. In addition, the HMVP table can be updated with motion information of all or a part of the CUs within the region that are coded based on the HMVP table.

In an embodiment, only motion information of the last K CUs, which are within the region and coded with the HMVP table, is used to update the HMVP table. K is an integer greater than 0. In an embodiment, only the last K motion information of the remaining motion information of the CUs, which are within the region and coded with the HMVP table, is used to update the HMVP table. The remaining motion information results from a pruning operation where the motion information identical or similar to other motion information is removed. For example, the region has a size of 32×32 pixels, and K is set to be 2 in one example. Accordingly, at most the motion information of the last 2 CUs within the region coded with the HMVP table is used for updating the HMVP table after the region is decoded. In another example, the region has a size of 64×64 pixels, and K is set to be 6.

In an embodiment, only motion information of the first J CUs within the region coded with the HMVP table is used to update the HMVP table. J is an integer greater than 0. In an embodiment, only the first J motion information of the remaining motion information of the CUs within the region coded with the HMVP table is used to update the HMVP table. The remaining motion information results from a pruning operation.

B. HMVP Table Resetting Techniques

In some embodiments, an HMVP table is reset after N CTU rows are processed, or at the beginning of every N CTU rows. N can be an integer greater than 0. For example, the HMVP table can be reset after every 1, 2, or 3 CTU rows are processed. The N CTU rows may include CUs that are processed based on the HMVP table or processed with a coding mode that does not use the HMVP table. The value of N can be predefined or can be signaled with a syntax element at sequence level, picture level, slice level, tile group level, tile level, or the like. Compared with resetting an HMVP table at the beginning of a slice, resetting an HMVP table for every N CTU rows may limit HMVP candidates to be within a range closer to a current CU. Accordingly, motion vector prediction can be performed more effectively by referring those HMVP candidates that are potentially more similar to motion vectors of the current CU.

Figures 5, 6:
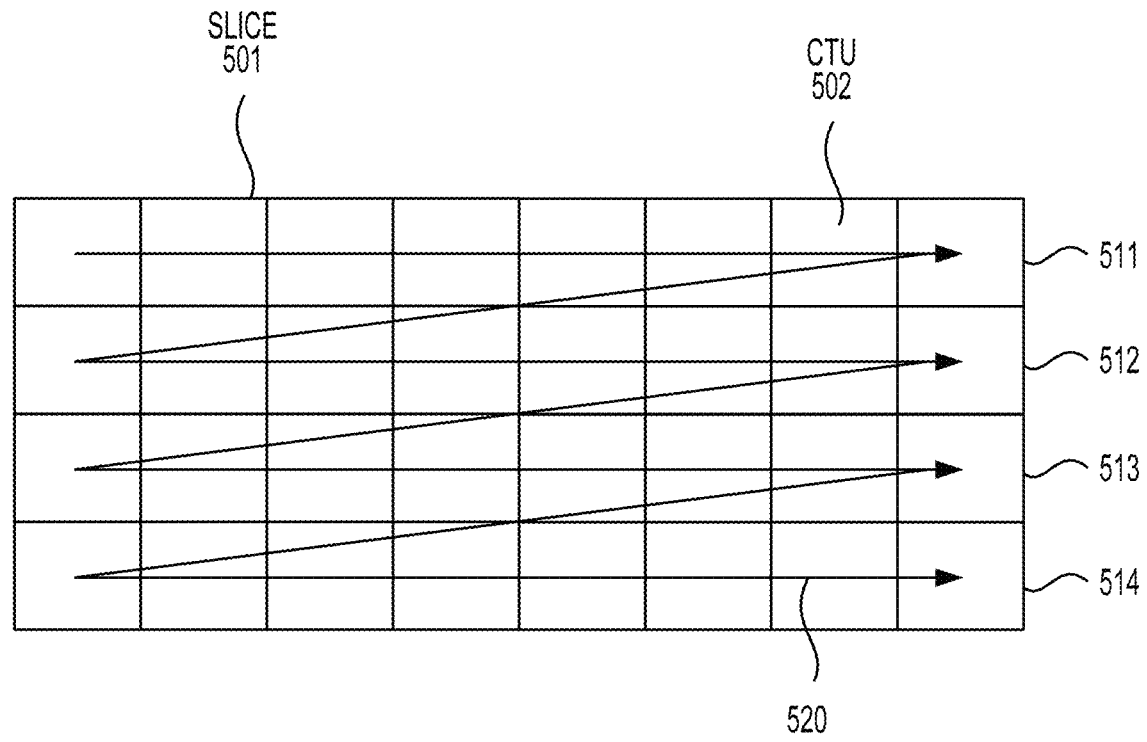
FIG. 5 shows a slice in a picture that includes 4 CTU rows.
FIG. 6 shows a tile in a picture that includes 4 CTU rows.

In one embodiment, the N CTU rows are partitioned from a slice, such as the slice specified in HEVC or VVC standards. As an example, FIG. 5 shows a slice 501 in a picture that includes 4 CTU rows 511-514 each including a row of CTUs 502. The CTU rows 511-514 can be processed sequentially in a raster scan order from CTU row 511 to CTU row 514 as indicated by arrows 520. An HMVP table used for processing the slice 501 can be reset at the beginning of each CTU row 511-514. Alternatively, the HMVP table used for processing the slice 501 can be reset at the beginning of every two CTU rows, for example, at the beginning of CTU rows 511 and 513.

In one embodiment, the N CTU rows are partitioned from a tile, such as the tile specified in HEVC or VVC standards. As an example, FIG. 6 shows a tile 601 in a picture that includes 4 CTU rows 611-614 each including a row of CTUs 602. The CTU rows 611-614 can be processed sequentially in a taster scan order from CTU row 611 to CTU row 614 as indicated by arrows 620. An HMVP table used for processing the tile 601 can be reset at the beginning of each CTU row 611-614. Alternatively, the HMVP table used for processing the tile 601 can be reset at the beginning of every two CTU rows, for example, at the beginning of CTU rows 611 and 613. A beginning of a tile is also a beginning of a first CTU row in a tile. Thus, when a picture is partitioned into a sequence of tiles, in one example, an HMVP table used for processing those tiles can be reset at the beginning of each tile.

In some embodiments, an HMVP table is reset after N CTUs are processed, or at the beginning of each set of N CTUs. Similarly, N can be an integer greater than 0. For example, the HMVP table can be reset after every 1, 2, or 3 CTUs are processed. The N CTUs may include CUs that are processed based on the HMVP table or processed with a coding mode that does not use the HMVP table. The value of N can be predefined or can be signaled with a syntax element at sequence level, picture level, slice level, tile group level, tile level, or the like.

In some embodiments, an HMVP table is reset after a region in a picture is processed, or at the beginning of each such region. For example, the regions may be partitioned from a picture for purpose of pipelined processing. The regions may have one or more predefined sizes (e.g., 32×32 or 64×64 pixels).

In various embodiments, when resetting an HMVP table, different resetting operations may be performed. For example, the HMVP table can be emptied, or HMVP candidates in the HMVP table are all marked as unavailable. Alternatively, the HMVP table may be initialized with certain motion information, for example, at the beginning of a CTU row, a tile, or a slice, such that there are HMVP candidates available for coding CUs after the resetting operation.

In one embodiment, the HMVP table for encoding or decoding a current CTU row can be initialized with motion information of one or more CUs in a CTU row above the current CTU row. For example, in FIG. 6 example, at the beginning of the CTU row 613, the HMVP table can be initialized with motion information of CUs within the CTU row 612. For example, the motion information of CUs in the above CTU row can be stored in a buffer.

In one example, the HMVP table for encoding or decoding the current CTU row is initialized with motion information of one or more CUs in first several CTUs in the CTU row above the current CTU row. In one example, the motion information of a last coded CU in the upper-right CTU of the first CTU in the current CTU row is inherited for the current CTU, and is used to initialize the HMVP table. In one example, the motion information of a bottom-left CU in the first CTU of the above CTU row is added to the HMVP table when resetting the HMVP table.

C. Multiple Buffers and Pruning Operations

In one embodiment, two HMVP tables are employed for processing a current CU. For example, a first HMVP table is configured to store motion information of last decoded CUs in an above CTU row, while a second HMVP table is configured to store motion information of CUs in a current CTU row. For example, the first HMVP table may be stored in a first buffer, and maintained after the above CTU row is decoded. The second HMVP table may be stored in a second buffer, initialized at the beginning of the current CTU row, and updated while the CUs in the current CTU row are processed.

Under such a configuration, a current CU in the current CTU row can be processed with reference to both the first and second HMVP tables. For example, an AMVP or merge list can be constructed for the current CU based on HMVP candidates from both HMVP tables according to certain rules. For example, when the HMVP candidates in the second HMVP table are not available or not enough (e.g., the first HMVP table is just reset), the HMVP candidates in the first HMVP table can be used. For example, HMVP candidates for constructing a candidate list may partially selected from the first HMVP table and partially selected from the second HMVP table.

In one embodiment, when adding a new HMVP candidate to an HMVP table, a pruning process is performed. For example, the new HMVP candidate is compared with all or a subset of HMVP candidates in the HMVP table. When an HMVP candidate identical or similar to the new candidate is found, the new candidate may not be added to the HMVP table. Performing such a pruning process over a subset of HMVP candidates in an HMVP table can reduce the complexity of updating the HMVP table and lower associated computation cost.

IV. HMVP Table Based Process

Figure 7:
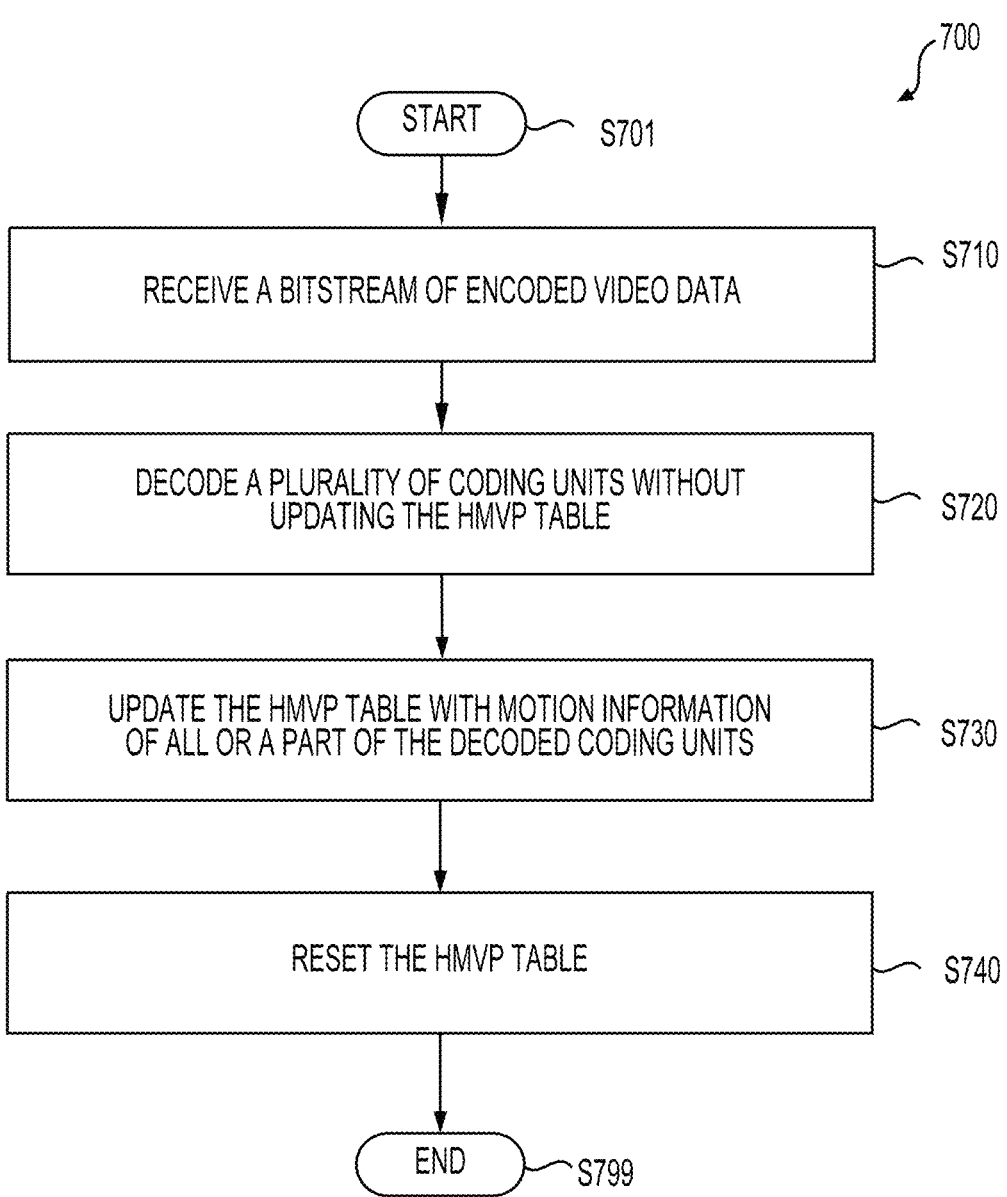
FIG. 7 shows a decoding process based on an HMVP table according to embodiments of the disclosure.

FIG. 7 shows a decoding process 700 according to embodiments of the disclosure. An HMVP table is employed in the process 700. The process 700 can be performed at the decoder 200. The process 700 starts from S701, and proceeds to S710.

At S710, a bitstream of encoded video data is received. The bitstream may include encoded data of a picture that is partitioned into CUs based on a tree-structure based partition scheme.

At S720, a plurality of CUs in the picture is decoded based on motion information stored in the HMVP table. However, updating of the HMVP table is performed after the plurality of the CUs is decoded instead of updating the HMVP table whenever one of the plurality of CUs is decoded based on the HMVP table.

At S730, the HMVP table is updated with motion information of all or a part of the plurality of CUs that is decoded based on the HMVP table. For example, the motion information of the last Q decoded CUs or the first W decoded CUs of the plurality of CUs can be used to update the HMVP table.

In an embodiment, the plurality of CUs is in a merge sharing region. The HMVP table is updated after the merge sharing region is processed.

At S740, the HMVP table is reset. For example, the resetting operation can be performed at the beginning of a CTU row in a slice or in a tile. The process 900 can proceed to S799 and terminates at S799.

While aspects of the present disclosure have been described in conjunction with the specific embodiments thereof that are proposed as examples, alternatives, modifications, and variations to the examples may be made. Accordingly, embodiments as set forth herein are intended to be illustrative and not limiting. There are changes that may be made without departing from the scope of the claims set forth below.

What is claimed is:

1. A method of video decoding at a decoder, comprising:
receiving a bitstream including encoded data of a picture;
decoding a plurality of coding units (CUs) in the picture according to a decoding order based on motion information stored in a history-based motion vector prediction (HMVP) table without updating the HMVP table; and
updating the HMVP table with the motion information of the last Q CUs of the plurality of CUs in the decoding order, Q being an integer greater than 0, wherein the decoding includes:
   decoding CUs within a merge sharing region based on the motion information stored in the HMVP table, wherein the plurality of CUs are the CUs within the merge sharing region that are decoded based on a shared merge candidate list, the shared merge candidate list being derived based on the motion information stored in the HMVP table, and
the updating includes:
   after the merge sharing region is decoded, updating the HMVP table with the motion information of the last Q CUs of the plurality of CUs that are within the merge sharing region.

2. The method of claim 1, wherein the updating includes:
updating the HMVP table with remaining motion information of the motion information of the last Q CUs of the plurality of CUs resulting from a pruning operation.

3. The method of claim 1, wherein the updating includes:
performing a pruning operation, wherein the motion information for updating the HMVP table is added as the last HMVP candidates in the HMVP table, and a HMVP candidate that is previously stored in the HMVP table and identical or similar to the respective motion information for updating the HMVP table is removed.

4. An apparatus of video decoding, comprising circuitry configured to:
receive a bitstream including encoded data of a picture,
decode a plurality of coding units (CUs) in the picture according to a decoding order based on motion information stored in a history-based motion vector prediction (HMVP) table without updating the HMVP table, and
update the HMVP table with the motion information of the last Q CUs of the plurality of CUs in the decoding order, Q being an integer greater than 0, wherein
the circuitry is further configured to:
   decode CUs within a merge sharing region based on the motion information stored in the HMVP table, wherein the plurality of CUs are the CUs within the merge sharing region that are decoded based on a shared merge candidate list, the shared merge candidate list being derived based on the motion information stored in the HMVP table, and
after the merge sharing region is decoded, update the HMVP table with the motion information of the last Q CUs of the plurality of CUs that are within the merge sharing region.

5. The apparatus of claim 4, wherein the circuitry is further configured to:
update the HMVP table with remaining motion information of the motion information of the last Q CUs of the plurality of CUs resulting from a pruning operation.

6. The apparatus of claim 4, wherein the circuitry is further configured to:
perform a pruning operation, wherein the motion information for updating the HMVP table is added as the last HMVP candidates in the HMVP table, and a HMVP candidate that is previously stored in the HMVP table and identical or similar to the respective motion information for updating the HMVP table is removed.

7. A non-transitory computer-readable medium storing instructions that, when executed by a processor, cause the processor to perform a method of video decoding, the method comprising:
receiving a bitstream including encoded data of a picture;
decoding a plurality of coding units (CUs) in the picture according to a decoding order based on motion information stored in a history-based motion vector prediction (HMVP) table without updating the HMVP table; and
updating the HMVP table with the motion information of the last Q CUs of the plurality of CUs in the decoding order, Q being an integer greater than 0, wherein
the decoding comprises:
   decoding CUs within a merge sharing region based on the motion information stored in the HMVP table, wherein the plurality of CUs are the CUs within the merge sharing region that are decoded based on a shared merge candidate list, the shared merge candidate list being derived based on the motion information stored in the HMVP table, and the updating includes:

after the merge sharing region is decoded, updating the HMVP table with the motion information of the last Q CUs of the plurality of CUs that are within the merge sharing region.

8. The non-transitory computer-readable medium of claim 7, wherein the updating further comprises:

updating the HMVP table with remaining motion information of the motion information of the last Q CUs of the plurality of CUs resulting from a pruning operation.

9. The non-transitory computer-readable medium of claim 7, wherein the updating comprises:

performing a pruning operation, wherein the motion information for updating the HMVP table is added as the last HMVP candidates in the HMVP table, and a HMVP candidate that is previously stored in the HMVP table and identical or similar to the respective motion information for updating the HMVP table is removed.

\* \* \* \* \*